United States Patent [19]
Hillman

[11] Patent Number: 5,917,028
[45] Date of Patent: Jun. 29, 1999

[54] HUMAN PHOSPHOPROTEIN

[75] Inventor: Jennifer L. Hillman, San Jose, Calif.

[73] Assignee: Incyte Pharmaceuticals, Inc., Palo Alto, Calif.

[21] Appl. No.: 08/739,484

[22] Filed: Oct. 29, 1996

[51] Int. Cl.[6] .............................. C12N 15/11; C12N 15/12
[52] U.S. Cl. ........................................ 536/23.5; 536/24.31
[58] Field of Search .............................. 536/23.5, 24.31; 435/320.1, 32.5, 252.3, 254.11, 69.1, 6

[56] References Cited

U.S. PATENT DOCUMENTS 5,656,654   8/1997   Buzzetti et al. ........................ 514/412

FOREIGN PATENT DOCUMENTS

93/16178   8/1993   WIPO .

OTHER PUBLICATIONS

Peyrollier, K., et al., "α Endosulfine is a novel molecule, structually related to a family of phosphoproteins," *Biochemical and Biophysical Research Communications*, 223:583–586 (1996).

EMEST Database entry Hsaa26133, Accession No. AA126133; Nov. 30, 1996, Hillier, L., et al., "Homo sapiens cDNA clone 511419 5 similar to TR:G162688 G1626588 cAMP–regulated phosphoprotein," XP002054125.

EMEST Database entry Hs56456, Accession No. T78564; Apr. 8, 1995, Hillier, L., et al., "Homo sapiens cDNA clone 72348 5' similar to SP:A35308, A35308 cAMP–regulated phosphoprotein, 16K," XP002054126.

Walaas, SI et al., "A dopamine– and cyclic AMP–regulated phosphoprotein enriched in dopamine–innervated brain regions" *Nature* 301:69–71 (1983).

Hemmings, HC et al., "DARPP–32, a dopamine–regulated neuronal phosphoprotein, is a potent inhibitor of protein phosphatase–1" *Nature* 310:503–505 (1984).

Halpain, S et al., "Activation of NMDA receptors induces dephosphorylation of DARPP–32 in rat striatal slices" *Nature* 343:369–372 (1990).

Horiuchi, A et al., "Purification and cDNA Cloning of ARPP–16, a cAMP–regulated Phosphoprotein Enriched in Basal Ganglia, and of a Related Phosphoprotein, ARPP–19" *J Biol Chem* 265(16) 9476–9484 (1990) (Accession GI 162690).

Girault, JA et al., "Differential Expression of ARPP–16 and ARPP–19, Two Highly Related cAMP–Regulated Phosphoproteins, One of Which Is Specifically Associated with Dopamine–Innervated Brain Regions" *J Neurosci* 10(4):1124–1133 (1990).

Brené, S et al., "Expression of mRNAs Encoding ARPP–16/19, ARPP–21, and DARPP–32 in Human Brain Tissue" *J Neurosci* 14(3):985–998 (1994) (Accession GI 741603).

Pincus, DW et al., "Vasoactive intestinal peptide regulation of neuroblast mitosis and survival: role of cAMP" *Brain Res* 514:355–357 (1990).

Girault, JA et al., "Regulation by cAMP and vasoactive intestinal peptide of phosphorylation of specific proteins in striatal cells in culture" *Proc. Natl. Acad. Sci.* 85:7790–7794 (1988).

*Primary Examiner*—Eric Grimes
*Attorney, Agent, or Firm*—Lucy J. Billings; Incyte Pharmaceuticals, Inc.

[57] ABSTRACT

The present invention provides a novel human phosphoprotein (hPSHP) and polynucleotides which identify and encode hPSHP. The invention also provides genetically engineered expression vectors and host cells comprising the nucleic acid sequences encoding hPSHP. The invention also provides pharmaceutical compositions containing hPSHP or agonists and antagonists to hPSHP, and in the use of these compositions for the treatment of diseases associated with hPSHP. Additionally, the invention provides for the use of antisense molecules to polynucleotides encoding hPSHP for the treatment of diseases associated with the expression of hPSHP. The invention also provides diagnostic assays which utilize the polynucleotide, or fragments or the complement thereof, to hybridize to the genomic sequence or transcripts of polynucleotides encoding hPSHP or anti hPSHP antibodies which specifically bind to hPSHP.

2 Claims, 6 Drawing Sheets

```
                    9        18        27        36        45        54
5' GTG AAT GGA AAG GGG ATG GCT GGT GGT CTT GGG TGT GAA TGT GTG TTA TTG GTT
                         M   A   G   L   G   C   E   C   V   L   L   V 63        72        81        90        99       108
    TGT AGA GGA CAC GCA GCA GCA AAG AAG GTA TTC TGC CTG AGA AGA GCT GAA GAG
     C   R   G   H   A   G   A   K   K   V   F   C   L   R   R   A   E   E 117       126       135       144       153       162
    GCA AAG CTA AAG GCC AAA TAC CCA AGC CTA GGA CAA AAG CCT GGA GGC TCC GAC
     A   K   L   K   A   K   Y   P   S   L   G   Q   K   P   G   G   S   D 171       180       189       198       207       216
    TTT CTC ATG AAG AGA CTC CAG AAA GGG CAA AAG TAC TTT GAC TCA GGA GAC TAC
     F   L   M   K   R   L   Q   K   G   Q   K   Y   F   D   S   G   D   Y 225       234       243       252       261       270
    AAC ATG GCC AAA GCC AAG ATG AAG AAT AAG CAG CTG CCA AGT GCA GGA CCA GAC
     N   M   A   K   A   K   M   K   N   K   Q   L   P   S   A   G   P   D 279       288       297       306       315       324
    AAG AAC CTG GTG ACT GGT GAT CAC ATC CCC ACC CCA CAG GAT CTG CCC CAG AGA
     K   N   L   V   T   G   D   H   I   P   T   P   Q   D   L   P   Q   R 333       342       351       360       369       378
    AAG TCC TCG CTC GTC ACC AAG CTT GCG GGT GGC CAA GTT GAA TGA TGC TGC
     K   S   S   L   V   T   S   K   L   A   G   G   Q   V   E 387       396       405       414       423       432
    CCG GGG CTC TGC CAG ATC CTG AGA CGC TTC CCC TCC CTG CNC CAC CCG GGT CCT 441       450
    GTG CTG GCT CCT GCC CCT TCC 3'
```

```
5' GTG AAT GGA AAG GGG ATG GCT GGT CTT GGG TGT GAA TGT GTG TTA TTG GTT
                                                                      54
                      M   A   G   L   G   C   E   C   V   L   L   V

TGT AGA GGA CAC GCA AAG GTA TTC TGC CTG AGA AGA GCT GAA GAG
 63                                                       108
 C   R   G   H   A   K   V   F   C   L   R   R   A   E   E

GCA AAG CTA AAG GCC AAA TAC CCA AGC CTA GGA CAA AAG CCT GGA GGC TCC GAC
117                                                                  162
 A   K   L   K   A   K   Y   P   S   L   G   Q   K   P   G   G   S   D

TTT CTC ATG AAG AGA CTC CAG AAA ATG AAG GGG CAA AAG TAC TTT GAC TCA GGA GAC TAC
171                                                                           216
 F   L   M   K   R   L   Q   K   M   K   G   Q   K   Y   F   D   S   G   D   Y

AAC ATG GCC AAA GCC AAA ATG AAG AAT AAG CAG CTG CCA CCA AGT GCA GGA CCA GAC
225                                                                       270
 N   M   A   K   A   K   M   K   N   K   Q   L   P   P   S   A   G   P   D

AAG AAC CTG GTG ACT GGT GAT CAC ATC CCC ACC CCA CAG GAT CTG CCC CAG AGA
279                                                                  324
 K   N   L   V   T   G   D   H   I   P   T   P   Q   D   L   P   Q   R

AAG TCC TCG CTC GTC ACC AGC AAG CTT GCG GGT CAA GTT GAA TGA TGC
333                                                          378
 K   S   S   L   V   T   S   K   L   A   G   Q   V   E   *   C
```

FIGURE 1A

```
      387             396             405             414             423             432
CCG GGG CTC TGC CAG ATC CTG AGA CGC TTC CCC TCC CTG CNC CAC CCG GGT CCT
      441             450
GTG CTG GCT CCT GCC CCT TCC 3'
```

FIGURE 1B

```
                                                          seq1
                                                          seq3
                                                          seq4
  1  M A G G L G C E C V L L V C R G H A G A K K V F C L R R A E E A K L K A K Y P S
  1  M S A E V P E A A S A E - - E Q K E M E D K V T S P E K A E E A K L K A R Y P H
  1  M - - - - - - - - - - - - - - - - - - - - E D K V T S P E K A E E A K L K A R Y P H seq1
                                                          seq3
                                                          seq4
 41  L G Q K P G G S D F L M K R L Q K G Q K Y F D S G D Y N M A K A K M K N K Q L P
 39  L G Q K P G G S D F L R K R L Q K G Q K Y F D S G D Y N M A K A K M K N K Q L P
 23  L G Q K P G G S D F L R K R L Q K G Q K Y F D S G D Y N M A K A K M K N K Q L P seq1
                                                          seq3
                                                          seq4
 81  S A G P D K N L V T G D H I P T P Q D L P Q R K S S L V T S K L A G G Q V E
 79  T A T P D K T E V T G D H I P T P Q D L P Q R K P S L V A S K L A G
 63  T A A P D K T E V T G D H I P T P Q D L P Q R K P S L V A S K L A G
```

HUMAN PHOSPHOPROTEIN

FIELD OF THE INVENTION

The present invention relates to the nucleic acid and amino acid sequences of a novel human phosphoprotein and to the use of these sequences in the study, diagnosis, treatment, and prevention of disease.

BACKGROUND OF THE INVENTION

Many hormones and neurotransmitters exert their actions on target cells by raising the levels of cAMP, which activates cAMP-dependent protein kinase. Activation of this kinase results in the phosphorylation of molecules which produces a variety of effects including the alteration of catalytic properties of enzymes, changes in the conductance of ion channels, and modification in the levels of expression of various genes. The effects produced upon a given hormone or neurotransmitter acting through cAMP depend on the cell type and the developmental stage of the cell. This specificity is due to the selective expression of only a few of all the possible substrates for cAMP-dependent protein kinase in any given cell. In order to define the mechanisms and specific functions of cAMP-mediated signal transduction in a particular cell type, it is necessary to identify the substrates for cAMP-dependent protein kinase in these cells.

An example of an extensively studied phosphoprotein is the dopamine and cAMP-regulated phosphoprotein DARPP-32 which is expressed in the cells of the rat brain caudate putamen that also express dopamine $D_1$ receptors (Walaas, S. I. (1983) Nature 301:69–71). The phosphatase-1 inhibitor function of DARPP-32 is dependent on its state of phosphorylation, which is regulated by receptor stimulation. Dopaminergic ($D_1$) and glutamatergic (NMDA) receptor stimulation both regulate the extent of DARPP-32 phosphorylation but in opposite directions. Dopamine $D_1$ receptor stimulation enhances cAMP formation resulting in the phosphorylation of DARPP-32, and phosphorylated DARPP-32 is a protein phosphatase-1 inhibitor. Glutamatergic NMDA receptor stimulation elevates intracellular calcium, leading to activation of calcineurin and dephosphorylation of phospho-DARPP-32, and reducing the phosphatase-1 inhibitory activity of DARPP-32 (Hemmings, H. C. (1984) Nature 310: 503–505, Halpain, S. (1990) Nature 343: 369–372). Therefore the normal levels of phosphorylated DARPP-32 in brain cells are dependent on a balance between the excitatory and inhibitory receptors and their respective neurotransmitters.

Another cAMP-regulated phosphoprotein which is highly enriched in the caudate putamen is ARPP-16. A related phosphoprotein, ARPP-19, was identified because it copurified with ARPP-16, has identical phosphorylation sites, and cross reacts with antibodies raised to ARPP-16 (Horiuchi, A. (1990) J Biol Chem 265 (16):9476–84). The amino acid sequences of ARPP-16 and ARPP-19 are identical except for an additional 16 amino acids at the $NH_2$-terminal of ARPP-19. The expression of these highly similar phosphoproteins has been examined in the rat and human brain and in peripheral organs (Girault, J. A. (1990) J Neurosci 10 (4):1124–1133, and Brene, S. (1994) J Neurosci 14 (3):985–998). ARPP-16 and ARPP-19 are present in the caudate putamen, globus pallidus, cerebral cortex, substantia nirga and nucleus accumbens, but ARPP-16 levels were found to be 2–3 times higher than ARPP-19 levels in the caudate putamen. ARPP-16 was only observed in the brain regions listed above and not in any peripheral organs, while ARPP-19 was found in all brain regions and in all peripheral organs tested.

Stimulation of the cAMP pathways has been found to enhance survival, differentiation, and mitosis in cultured neuroblasts, indicating that the cAMP-dependent pathways have a role in the regulation of neuronal development (Pincus, D. W. (1990) Brain Res 514: 355–357). Similarly, tissues that are not terminally differentiated such as a variety of tumor-derived cell lines contained ARPP-19 in similar or greater levels than normal tissue, while ARPP-16 was not found in any of them (Girault, supra).

The developmental expression of ARPP-16 and ARPP-19 has been studied in mouse brain and peripheral organs. ARPP-16 appears at the end of the first post-natal week in brain structures, increases until eight weeks in the caudate putamen, and then plateaus, while ARPP-19 levels are highest in embryo tissues and decrease with development in all regions examined (Girault, supra). In spite of the high degree of sequence identity between these two molecules these results indicate that they have different and very distinct functions; ARPP-19 is associated with cells that are not fully differentiated and plays a role in more ubiquitous cell development processes while ARPP-16 is specifically expressed in brain tissues that express dopamine receptors.

Many disorders of movement, such as Parkinson's and Huntington's diseases, have been attributed to disturbances of the basal ganglia structures within the brain including the caudate putamen. These diseases involve selective loss of specific neurons which results in an imbalance between excitatory and inhibitory neurotransmittors and their receptors. Current drug therapies attempt to restore this balance, but until the mechanisms of these disease processes are more fully understood, more effective treatments will not be available. The discovery of the polynucleotide sequence encoding the novel human phosphoprotein protein associated with cell development, regulation of neurotransmitters, and signal transduction presents the opportunity to investigate the mechanisms of diseases associated with these processes. Discovery of molecules related to a novel human phosphoprotein protein would satisfy a need in the art by providing a new means for the diagnosis, prevention, treatment, or study of degenerative brain diseases and abnormal cell death and proliferation.

SUMMARY OF THE INVENTION

The present invention features a novel human phosphoprotein hereinafter designated as hPSHP and characterized as having similarity to two phosphoproteins, GI 162690 and GI 741603.

Accordingly, the invention features a substantially purified hPSHP having chemical homology to phosphoproteins above and as shown in the amino acid sequence of SEQ ID NO:1.

One aspect of the invention features isolated and substantially purified polynucleotides that encode hPSHP. In a particular aspect, the polynucleotide is the nucleotide sequence of SEQ ID NO:2.

The invention also relates to a polynucleotide sequence comprising the complement of SEQ ID NO:2 or variants thereof. In addition, the invention features polynucleotide sequences which hybridize under stringent conditions to SEQ ID NO:2.

The invention additionally features nucleic acid sequences encoding polypeptides, oligonucleotides, peptide nucleic acids (PNA), fragments, portions or antisense molecules thereof, and expression vectors and host cells comprising polynucleotides that encode hPSHP. The present invention also features antibodies which bind specifically to a hPSHP, and pharmaceutical compositions comprising substantially purified hPSHP.

BRIEF DESCRIPTION OF THE FIGURES

FIG. 1 shows the amino acid sequence (SEQ ID NO:1) and nucleic acid sequence (SEQ ID NO:2) of hPSHP. The alignment was produced using MacDNASIS PRO™ software (Hitachi Software Engineering Co., Ltd, San Bruno, Calif.).

FIG. 2 shows the amino acid sequence alignments among hPSHP (SEQ ID NO:1), GI 162690 (SEQ ID NO:3), and GI 741603 (SEQ ID NO:4). The alignment was produced using the multisequence alignment program of DNASTAR™ software (DNASTAR Inc, Madison Wis.).

DESCRIPTION OF THE INVENTION

Figure 3:
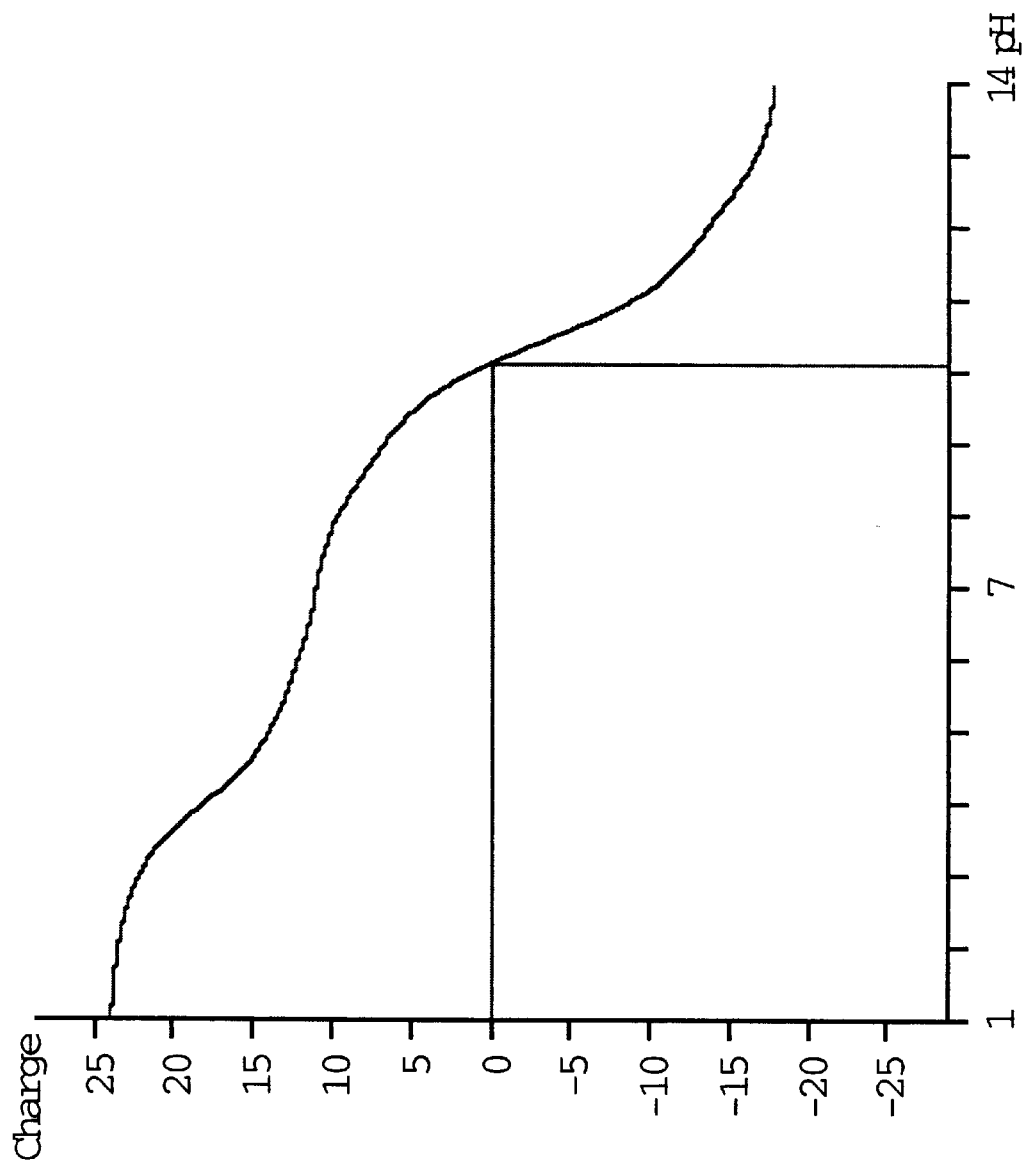
FIG. 3 shows the isoelectric plot (generated using MacDNASIS PRO software) for hPSHP (SEQ ID NO:1).

Before the present protein, nucleotide sequence, and methods are described, it is understood that this invention is not limited to the particular methodology, protocols, cell lines, vectors, and reagents described as these may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

DEFINITIONS

"Nucleic acid sequence" as used herein refers to an oligonucleotide, nucleotide, or polynucleotide, and fragments or portions thereof, and to DNA or RNA of genomic or synthetic origin which may be single-or double-stranded, and represent the sense or antisense strand. Similarly, "amino acid sequence" as used herein refers to an oligopeptide, peptide, polypeptide, or protein sequence and fragments or portions thereof, of a naturally occurring or synthetic molecule.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

"Peptide nucleic acid", as used herein, refers to a molecule which comprises an oligomer to which an amino acid residue, such as lysine, and an amino group have been added. These small molecules, also designated anti-gene agents, stop transcript elongation by binding to their complementary strand of nucleic acid (Nielsen, P. E. et al. (1993) Anticancer Drug Des. 8:53–63).

hPSHP, as used herein, refers to the amino acid sequences of substantially purified hPSHP obtained from any species, particularly mammalian, including bovine, ovine, porcine, murine, equine, and preferably human, from any source whether natural, synthetic, semi-synthetic, or recombinant.

"Consensus", as used herein, refers to a nucleic acid sequence which has been resequenced to resolve uncalled bases, or which has been extended using XL-PCR™ (Perkin Elmer, Norwalk, Conn.) in the 5' and/or the 3' direction and resequenced, or which has been assembled from the overlapping sequences of more than one Incyte clone using the GCG Fragment Assembly™ system (GCG, Madison, Wis.), or which has been both extended and assembled.

A "variant" of hPSHP, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Similar minor variations may also include amino acid deletions or insertions, or both. Guidance in determining which amino acid residues may be substituted, inserted, or deleted without abolishing biological or immunological activity may be found using computer programs well known in the art, for example, DNASTAR software.

A "deletion", as used herein, refers to a change in either amino acid or nucleotide sequence in which one or more amino acid or nucleotide residues, respectively, are absent.

An "insertion" or "addition", as used herein, refers to a change in an amino acid or nucleotide sequence resulting in the addition of one or more amino acid or nucleotide residues, respectively, as compared to the naturally occurring molecule.

A "substitution", as used herein, refers to the replacement of one or more amino acids or nucleotides by different amino acids or nucleotides, respectively.

The term "biologically active", as used herein, refers to a protein having structural, regulatory, or biochemical functions of a naturally occurring molecule. Likewise, "immunologically active" refers to the capability of the natural, recombinant, or synthetic hPSHP, or any oligopeptide thereof, to induce a specific immune response in appropriate animals or cells and to bind with specific antibodies.

The term "agonist", as used herein, refers to a molecule which, when bound to hPSHP, causes a change in hPSHP which modulates the activity of hPSHP. Agonists may include proteins, nucleic acids, carbohydrates, or any other molecules which bind to hPSHP.

The terms "antagonist" or "inhibitor", as used herein, refers to a molecule which, when bound to hPSHP, blocks the biological or immunological activity of hPSHP. Antagonists and inhibitors may include proteins, nucleic acids, carbohydrates, or any other molecules which bind to hPSHP.

The term "modulate", as used herein, refers to a change or an alteration in the biological activity of hPSHP. Modulation may be an increase or a decrease in protein activity, a change in binding characteristics, or any other change in the biological, functional, or immunological properties of hPSHP.

The term "mimetic", as used herein, refers to a molecule, the structure of which is developed from knowledge of the structure of hPSHP or portions thereof and, as such, is able to effect some or all of the actions of the hPSHP-like molecules.

The term "derivative", as used herein, refers to the chemical modification of a nucleic acid encoding hPSHP or the encoded hPSHP. Illustrative of such modifications would be replacement of hydrogen by an alkyl, acyl, or amino group. A nucleic acid derivative would encode a polypeptide which retains essential biological characteristics of the natural molecule.

The term "substantially purified", as used herein, refers to nucleic or amino acid sequences that are removed from their natural environment, isolated or separated, and are at least 60% free, preferably 75% free, and most preferably 90% free from other components with which they are naturally associated.

"Amplification" as used herein refers to the production of additional copies of a nucleic acid sequence and is generally carried out using polymerase chain reaction (PCR) technologies well known in the art (Dieffenbach, C. W.and G. S. Dveksler (1995) *PCR Primer, a Laboratory Manual,* Cold Spring Harbor Press, Plainview, N.Y.).

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., membranes, filters, chips, pins or glass slides to which cells have been fixed for in situ hybridization).

The terms "complementary" or "complementarity", as used herein, refer to the natural binding of polynucleotides under permissive salt and temperature conditions by base-pairing. For example, for the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between the nucleic acids strands.

The term "homology", as used herein, refers to a degree of complementarity. There may be partial homology or complete homology (i.e., identity). A partially complementary sequence is one that at least partially inhibits an identical sequence from hybridizing to a target nucleic acid; it is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or probe will compete for and inhibit the binding (i.e., the hybridization) of a completely homologous sequence or probe to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity); in the absence of non-specific binding the probe will not hybridize to the second non-complementary target sequence.

As known in the art, numerous equivalent conditions may be employed to comprise either low or high stringency conditions. Factors such as the length and nature (DNA, RNA, base composition) of the sequence, nature of the target (DNA, RNA, base composition, presence in solution or immobilization, etc.), and the concentration of the salts and other components (e.g., the presence or absence of formamide, dextran sulfate and/or polyethylene glycol) are considered and the hybridization solution may be varied to generate conditions of either low or high stringency different from, but equivalent to, the above listed conditions.

The term "stringent conditions", as used herein, is the "stringency" which occurs within a range from about Tm-5° C. (5° C. below the melting temperature (Tm) of the probe) to about 20° C. to 25° C. below Tm. As will be understood by those of skill in the art, the stringency of hybridization may be altered in order to identify or detect identical or related polynucleotide sequences.

The term "antisense", as used herein, refers to nucleotide sequences which are complementary to a specific DNA or RNA sequence. The term "antisense strand" is used in reference to a nucleic acid strand that is complementary to the "sense" strand. Antisense molecules may be produced by any method, including synthesis by ligating the gene(s) of interest in a reverse orientation to a viral promoter which permits the synthesis of a complementary strand. Once introduced into a cell, this transcribed strand combines with natural mRNA produced by the cell to form duplexes. These duplexes then block either the further transcription of the mRNA or its translation. In this manner, mutant phenotypes may be generated. The term "antisense strand" is used in reference to a nucleic acid strand that is complementary to the "sense" strand. The designation "negative" is sometimes used in reference to the antisense strand, and "positive" is sometimes used in reference to the sense strand.

The term "portion", as used herein, with regard to a protein (as in "a portion of a given protein") refers to fragments of that protein. The fragments may range in size from four amino acid residues to the entire amino acid sequence minus one amino acid. Thus, a protein "comprising at least a portion of the amino acid sequence of SEQ ID NO:1" encompasses the full-length human hPSHP and fragments thereof.

"Transformation", as defined herein, describes a process by which exogenous DNA enters and changes a recipient cell. It may occur under natural or artificial conditions using various method well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host cell chromosome. They also include cells which transiently express the inserted DNA or RNA for limited periods of time.

The term "antigenic determinant", as used herein, refers to that portion of a molecule that makes contact with a particular antibody (i.e., an epitope). When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The terms "specific binding" or "specifically binding", as used herein, in reference to the interaction of an antibody and a protein or peptide, mean that the interaction is dependent upon the presence of a particular structure (i.e., the antigenic determinant or epitope) on the protein; in other words, the antibody is recognizing and binding to a specific protein structure rather than to proteins in general. For example, if an antibody is specific for epitope "A", the presence of a protein containing epitope A (or free, unlabeled A) in a reaction containing labeled "A" and the antibody will reduce the amount of labeled A bound to the antibody.

The term "sample", as used herein, is used in its broadest sense. A biological sample suspected of containing nucleic acid encoding hPSHP or fragments thereof may comprise a cell, chromosomes isolated from a cell (e.g., a spread of metaphase chromosomes), genomic DNA (in solution or bound to a solid support such as for Southern blot analysis), RNA (in solution or bound to a solid support such as for northern blot analysis), cDNA (in solution or bound to a solid support), extract from cells or a tissue, and the like.

The term "correlates with expression of a polynucleotide", as used herein, indicates that the detection of the presence of ribonucleic acid that is complementary to SEQ ID NO:2 by northern analysis hybridization assays is indicative of the presence of mRNA encoding hPSHP in a sample and thereby correlates with expression of the transcript from the gene encoding the protein.

"Alterations" in the polynucleotide of SEQ ID NO:2, as used herein, comprise any alteration in the sequence of polynucleotides encoding hPSHP including deletions, insertions, and point mutations that may be detected using hybridization assays. Included within this definition is the detection of alterations to the genomic DNA sequence which encodes hPSHP (e.g., by alterations in the pattern of restriction fragment length polymorphisms capable of hybridizing to SEQ ID NO:2), the inability of a selected fragment of SEQ ID NO:2 to hybridize to a sample of genomic DNA (e.g., using allele-specific oligonucleotide probes), and improper or unexpected hybridization, such as hybridization to a locus other than the normal chromosomal locus for the gene encoding hPSHP (e.g., using fluorescent in situ hybridization [FISH] to metaphase chromosomes spreads).

As used herein, the term "antibody" refers to intact molecules as well as fragments thereof, such as Fa, F(ab')$_2$, and Fv, which are capable of binding the epitopic determinant. Antibodies that bind hPSHP polypeptides can be prepared using intact polypeptides or fragments containing small peptides of interest as the immunizing antigen. The polypeptide or peptide used to immunize an animal can be derived from translated cDNA or synthesized chemically, and can be conjugated to a carrier protein, if desired. Commonly used carriers that are chemically coupled to peptides include bovine serum albumin and thyroglobulin. The coupled peptide is then used to immunize the animal (e.g., a mouse, a rat, or a rabbit).

The term "humanized antibody", as used herein, refers to antibody molecules in which amino acids have been replaced in the non-antigen binding regions in order to more closely resemble a human antibody, while still retaining the original binding ability.

THE INVENTION

The invention is based on the discovery of a novel human phosphoprotein, hPSHP, the polynucleotides encoding hPSHP, and the use of these compositions for the diagnosis, prevention, or treatment of disorders of neurotransmitter regulation and signal transduction including Huntington's disease and Parkinson's disease, and conditions of abnormal cell death or proliferation.

Nucleic acids encoding the human hPSHP of the present invention were first identified in Incyte Clone No. 258512 from a retinoic acid treated hNT2 teratocarcinoma cell line cDNA library (HNT2RAT01) through a computer-generated search for amino acid sequence alignments. A consensus sequence, SEQ ID NO:2, was derived from the following overlapping and/or extended nucleic acid sequences: Incyte Clones 258512, 483293, 483619, 485751, and 486742 (HNT2RAT01); 841590 (PROSNOT05); 1613311 (COLNTUT06); 918496 (BRSTNOT04); 1518226 (BLADTUT04); and 1509755 (LUNGNOT14).

Figure 4:
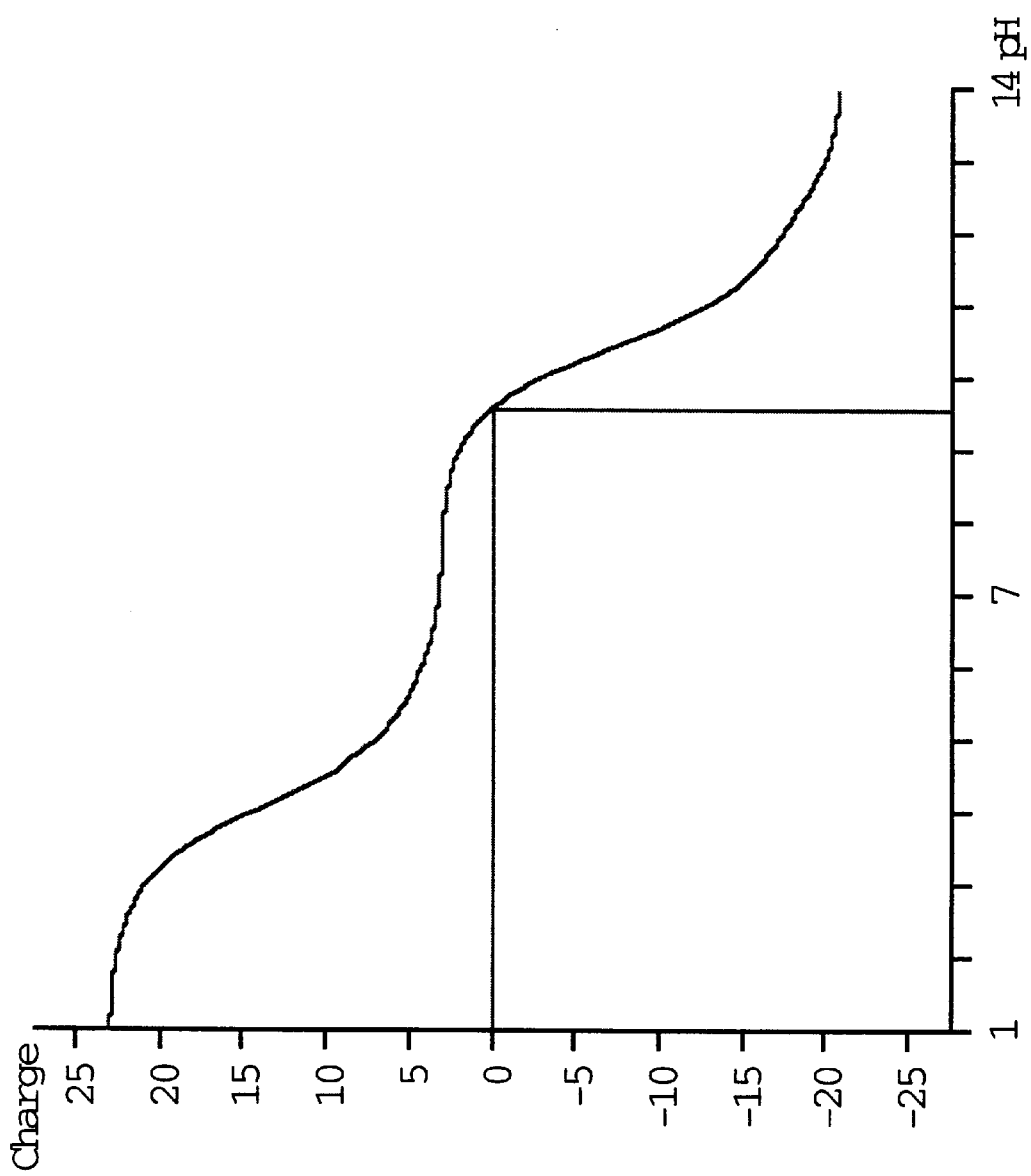
FIG. 4 shows the isoelectric plot (MacDNASIS PRO software) for SEQ ID NO:3.
Figure 5:
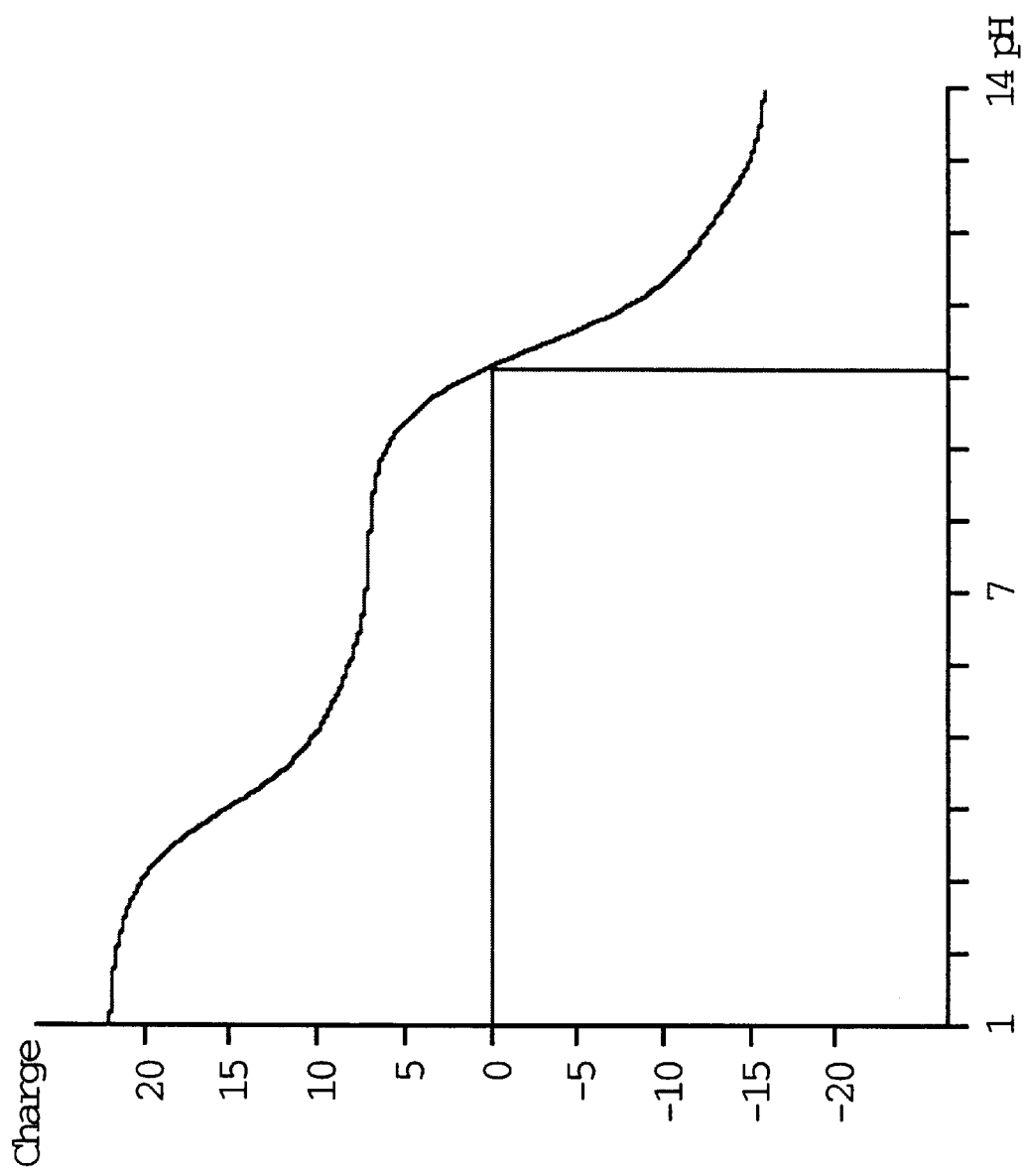
FIG. 5 shows the isoelectric plot (MacDNASIS PRO software) for SEQ ID NO:4.

In one embodiment, the invention encompasses a novel human phosphoprotein, a polypeptide comprising the amino acid sequence of SEQ ID NO:1, as shown in FIG. 1. hPSHP is 118 amino acids in length. hPSHP has chemical and structural homology with GI 162690 and GI 741603 as shown in FIG. 2. In particular, hPSHP and GI 162690 share 71% identity, whereas hPSHP and GI 741603 share 83% identity (FIG. 2). As illustrated by FIGS. 3, 4, and 5, hPSHP, GI 162690, and GI 741603 also have similar isoelectric points.

The invention also encompasses hPSHP variants. A preferred hPSHP variant is one having at least 80%, and more preferably 90%, amino acid sequence similarity to the hPSHP amino acid sequence (SEQ ID NO:1). A most preferred hPSHP variant is one having at least 95% amino acid sequence similarity to SEQ ID NO:1.

The invention also encompasses polynucleotides which encode hPSHP. Accordingly, any nucleic acid sequence which encodes the amino acid sequence of hPSHP can be used to generate recombinant molecules which express hPSHP. In a particular embodiment, the invention encompasses the polynucleotide comprising the nucleic acid of SEQ ID NO:2, as shown in FIG. 1.

It will be appreciated by those skilled in the art that as a result of the degeneracy of the genetic code, a multitude of nucleotide sequences encoding hPSHP, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring hPSHP, and all such variations are to be considered as being specifically disclosed.

Although nucleotide sequences which encode hPSHP and its variants are preferably capable of hybridizing to the nucleotide sequence of the naturally occurring hPSHP under appropriately selected conditions of stringency, it may be advantageous to produce nucleotide sequences encoding hPSHP or its derivatives possessing a substantially different codon usage. Codons may be selected to increase the rate at which expression of the peptide occurs in a particular prokaryotic or eukaryotic expression host in accordance with the frequency with which particular codons are utilized by the host. Other reasons for substantially altering the nucleotide sequence encoding hPSHP and its derivatives without altering the encoded amino acid sequences include the production of RNA transcripts having more desirable properties, such as a greater half-life, than transcripts produced from the naturally occurring sequence.

The invention also encompasses production of a DNA sequence, or portions thereof, which encode hPSHP and its derivatives, entirely by synthetic chemistry. After production, the synthetic gene may be inserted into any of the many available DNA vectors and cell systems using reagents that are well known in the art at the time of the filing of this application. Moreover, synthetic chemistry may be used to introduce mutations into a sequence encoding hPSHP or any portion thereof.

Also encompassed by the invention are polynucleotide sequences that are capable of hybridizing to the claimed nucleotide sequences, and in particular, those shown in SEQ ID NO:2 under various conditions of stringency. Hybridization conditions are based on the melting temperature (Tm) of the nucleic acid binding complex or probe, as taught in Berger and Kimmel (1987; Methods in Enzymol., Vol. 152, Academic Press, San Diego, Calif.), and may be used at a defined stringency.

Altered nucleic acid sequences encoding hPSHP which are encompassed by the invention include deletions, insertions, or substitutions of different nucleotides resulting in a polynucleotide that encodes the same or a functionally equivalent hPSHP. The encoded protein may also contain deletions, insertions, or substitutions of amino acid residues which produce a silent change and result in a functionally equivalent hPSHP. Deliberate amino acid substitutions may be made on the basis of similarity in polarity, charge, solubility, hydrophobicity, hydrophilicity, and/or the amphipathic nature of the residues as long as the biological activity of hPSHP is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine; glycine and alanine; asparagine and glutamine; serine and threonine; phenylalanine and tyrosine.

Also included within the scope of the present invention are encoded alleles of the gene encoding hPSHP. As used herein, an "allele" or "allelic sequence" is an alternative form of the gene which may result from at least one mutation in the nucleic acid sequence. Alleles may result in altered mRNAs or polypeptides whose structure or function may or may not be altered. Any given gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

Methods for DNA sequencing which are well known and generally available in the art may be used to practice any embodiments of the invention. The methods may employ such enzymes as the Klenow fragment of DNA polymerase I, Sequenase® (US Biochemical Corp, Cleveland, Ohio), Taq polymerase (Perkin Elmer), thermostable T7 polymerase (Amersham, Chicago, Ill.), or combinations of recombinant polymerases and proofreading exonucleases such as the ELONGASE Amplification System marketed by Gibco BRL (Gaithersburg, Md.). Preferably, the process is automated with machines such as the Hamilton Micro Lab 2200 (Hamilton, Reno, Nev.), Peltier Thermal Cycler (PTC200; MJ Research, Watertown, Mass.) and the ABI 377 DNA sequencers (Perkin Elmer).

The polynucleotide sequence encoding hPSHP may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Gobinda et al. (1993); PCR Methods Applic. 2:318–322). In particular, genomic DNA is first amplified in the presence of primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia T. et al. (1988) Nucleic Acids Res. 16:8186). The primers may be designed using OLIGO® 4.06 primer analysis software (National Biosciences Inc., Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom et al. (1991) PCR Methods Applic. 1:111–119). In this method, multiple restriction enzyme digestions and ligations may also be used to place an engineered double-stranded sequence into an unknown portion of the DNA molecule before performing PCR.

Another method which may be used to retrieve unknown sequences is that of Parker, J. D. et al. (1991; Nucleic Acids Res. 19:3055–3060). Additionally, one may use PCR, nested primers, and PromoterFinder™ libraries to walk in genomic DNA (Clontech, Palo Alto, Calif.). This process avoids the need to screen libraries and may be useful in finding intron/exon junctions.

When screening for full-length cDNAs, it is preferable to use libraries that have been size-selected to include larger cDNAs. Also, random-primed libraries are preferable in that they will contain more sequences which contain the 5' regions of genes. Use of a randomly primed library may be especially preferable for situations in which an oligo d(T) library does not yield a full-length cDNA. Genomic libraries may be useful for extension of sequence into the 5' and 3' non-translated regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled devise camera. Output/light intensity may be converted to electrical signal using appropriate software (e.g. Genotyper™ and Sequence Navigator™ from Perkin Elmer) and the entire process from loading of samples to computer analysis and electronic data display may be computer controlled.

Capillary electrophoresis is especially preferable for the sequencing of small pieces of DNA which might be present in limited amounts in a particular sample.

In another embodiment of the invention, polynucleotide sequences or fragments thereof which encode hPSHP, or fusion proteins or functional equivalents thereof, may be used in recombinant DNA molecules to direct expression of hPSHP in appropriate host cells. Due to the inherent degeneracy of the genetic code, other DNA sequences which encode substantially the same or a functionally equivalent amino acid sequence may be produced and these sequences may be used to clone and express hPSHP.

As will be understood by those of skill in the art, it may be advantageous to produce hPSHP-encoding nucleotide sequences possessing non-naturally occurring codons. For example, codons preferred by a particular prokaryotic or eukaryotic host can be selected to increase the rate of hPSHP expression or to produce a recombinant RNA transcript having desirable properties, such as a half-life which is longer than that of a transcript generated from the naturally occurring sequence.

The nucleotide sequences of the present invention can be engineered using methods generally known in the art in order to alter the hPSHP coding sequence for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequence. For example, site-directed mutagenesis may be used to insert new restriction sites, alter glycosylation patterns, to change codon preference, to produce splice variants, or other mutations, and so forth.

In another embodiment of the invention, a natural, modified, or recombinant polynucleotide encoding hPSHP may be ligated to a heterologous sequence to encode a fusion protein. For example, to screen peptide libraries for inhibitors of hPSHP activity, it may be useful to encode a chimeric hPSHP protein that can be recognized by a commercially available antibody. A fusion protein may also be engineered to contain a cleavage site located between a hPSHP encoding sequence and the heterologous protein sequence, so that the hPSHP may be cleaved and purified away from the heterologous moiety.

In another embodiment, the coding sequence of hPSHP may be synthesized, in whole or in part, using chemical methods well known in the art (see Caruthers, M. H. et al. (1980) Nucl. Acids Res. Symp. Ser. 215–223, Horn, T. et al. (1980) Nucl. Acids Res. Symp. Ser. 225–232, etc). Alternatively, the protein itself may be produced using chemical methods to synthesize the hPSHP amino acid sequence, or a portion thereof. For example, peptide synthesis can be performed using various solid-phase techniques (Roberge J. Y. et al. (1995) Science 269:202–204) and automated synthesis may be achieved, for example, using the ABI 431A Peptide Synthesizer (Perkin Elmer).

The newly synthesized peptide may be substantially purified by preparative high performance liquid chromatography (e.g., Creighton T. (1983) *Proteins, Structures and Molecular Principles,* W. H. Freeman and Co., New York, N.Y.). The composition of the synthetic peptides may be confirmed by amino acid analysis or sequencing (e.g., the Edman degradation procedure; Creighton, supra). Additionally, the amino acid sequence of hPSHP, or any part thereof, may be altered during direct synthesis and/or combined using chemical methods with sequences from other proteins, or any part thereof, to produce a variant polypeptide.

In order to express a biologically active hPSHP, the nucleotide sequence encoding hPSHP or functional equivalents, may be inserted into an appropriate expression vector, i.e., a vector which contains the necessary elements for the transcription and translation of the inserted coding sequence.

Methods which are well known to those skilled in the art may be used to construct expression vectors containing a hPSHP coding sequence and appropriate transcriptional and translational control elements. These methods include in vitro recombinant DNA techniques, synthetic techniques, and in vivo recombination or genetic recombination. Such techniques are described in Sambrook, J. et al. (1989) *Molecular Cloning, A Laboratory* Manual, Cold Spring Harbor Press, Plainview, N.Y., and Ausubel, F. M. et al. (1989) *Current Protocols in Molecular Biology,* John Wiley & Sons, New York, N.Y.

A variety of expression vector/host systems may be utilized to contain and express a hPSHP coding sequence. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or transformed with bacterial expression vectors (e.g., Ti or pBR322 plasmid); or animal cell systems.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the Bluescript® phagemid (Stratagene, LaJolla, Calif.) or pSport1 (Gibco BRL) and ptrp-lac hybrids, and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding hPSHP, vectors based on SV40 or EBV may be used with an appropriate selectable marker.

In bacterial systems, a number of expression vectors may be selected depending upon the use intended for hPSHP. For example, when large quantities of hPSHP are needed for the induction of antibodies, vectors which direct high level expression of fusion proteins that are readily purified may be used. Such vectors include, but are not limited to, the multifunctional *E. coli* cloning and expression vectors such as Bluescript® (Stratagene), in which the hPSHP coding sequence may be ligated into the vector in frame with sequences for the amino-terminal Met and the subsequent 7 residues of β-galactosidase so that a hybrid protein is produced; pIN vectors (Van Heeke, G. & S. M. Schuster (1989) J. Biol. Chem. 264:5503–5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, Saccharomyces cerevisiae, a number of vectors containing constitutive or inducible promoters such as alpha factor, alcohol oxidase, and PGH may be used. For reviews, see Ausubel et al. (supra) and Grant et al. (1987) Methods in Enzymology 153:516–544.

In cases where plant expression vectors are used, the expression of a sequence encoding hPSHP may be driven by any of a number of promoters. For example, viral promoters such as the 35S and 19S promoters of CaMV may be used alone or in combination with the omega leader sequence from TMV (Takamatsu et al. (1987) EMBO J. 6:307–311; Brisson et al. (1984) Nature 310:511–514). Alternatively, plant promoters such as the small subunit of RUBISCO; or heat shock promoters may be used (Coruzzi et al. (1984) EMBO J. 3:1671–1680; Broglie et al. (1984) Science 224:838–843; Winter, J. et al. (1991) Results Probl. Cell Differ. 17:85–105). These constructs can be introduced into plant cells by direct DNA transformation or pathogen-mediated transfection. Such techniques are described in a number of generally available reviews (see, for example, Hobbs, S. or Murry, L. E. in McGraw Hill *Yearbook of Science and Technology* (1992) McGraw Hill, New York, N.Y.; pp. 191–196 or Weissbach and Weissbach (1988) *Methods for Plant Molecular Biology*, Academic Press, New York, N.Y.; pp. 421–463).

In insect system may also be used to express hPSHP. For example, in one such system, *Autographa californica* nuclear polyhedrosis virus (AcNPV) is used as a vector to express foreign genes in *Spodoptera frugiperda* cells or in Trichoplusia larvae. The hPSHP coding sequence may be cloned into a non-essential region of the virus, such as the polyhedrin gene, and placed under control of the polyhedrin promoter. Successful insertion of hPSHP will render the polyhedrin gene inactive and produce recombinant virus lacking coat protein. The recombinant viruses may then be used to infect, for example, *S. frugiperda* cells or Trichoplusia larvae in which hPSHP may be expressed (Smith et al. (1983) J. Virol 46:584; Engelhard, E. K. et al. (1994) Proc. Nat. Acad. Sci. 91:3224–3227).

In mammalian host cells, a number of viral-based expression systems may be utilized. In cases where an adenovirus is used as an expression vector, a hPSHP coding sequence may be ligated into an adenovirus transcription/translation complex consisting of the late promoter and tripartite leader sequence. Insertion in a non-essential E1 or E3 region of the viral genome may be used to obtain a viable virus which is capable of expressing hPSHP in infected host cells (Logan and Shenk (1984) Proc. Natl. Acad. Sci. 81:3655–3659). In addition, transcription enhancers, such as the Rous sarcoma virus (RSV) enhancer, may be used to increase expression in mammalian host cells.

Specific initiation signals may also be used to achieve more efficient translation of a sequence encoding hPSHP sequence. Such signals include the ATG initiation codon and adjacent sequences. In cases where sequences encoding hPSHP, its initiation codon, and upstream sequences are inserted into the appropriate expression vector, no additional transcriptional or translational control signals may be needed. However, in cases where only coding sequence, or a portion thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20:125–162; Bittner et al. (1987) Methods in Enzymol. 153:516–544).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells such as CHO, HeLa, MDCK, HEK293, and WI38, which have specific cellular machinery and characteristic mechanisms for such post-translational activities, may be chosen to ensure the correct modification and processing of the introduced foreign protein.

For long-term, high-yield production of recombinant proteins, stable expression is preferred. For example, cell lines which stably express hPSHP may be transformed using expression vectors which may contain viral origins of replication and/or endogenous expression elements and a selectable marker gene on the same or separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase (Wigler, M. et al. (1977) Cell 11:223–32) and adenine phosphoribosyltransferase (Lowy, I. et al. (1980) Cell 22:817–823) genes which can be employed in tk- or aprt-cells, respectively. Also, antimetabolite, antibiotic, or herbicide resistance may be used as the basis for selection. For example, dhfr, which confers resistance to methotrexate (Wigler et al. (1980) Proc. Natl. Acad. Sci. 77:3567–3570); npt, which confers resistance to the aminoglycosides neomycin and G-418 (Colbere-Garapin et al. (1981) J. Mol. Biol. 150:1–14), and als or pat, which confer resistance to chlorsulfuron and phosphinotricin acetyltransferase, respectively (Murry, supra). Additional selectable genes may be used, for example, trpB, which allows cells to utilize indole in place of tryptophan, or hisD, which allows cells to utilize histinol in place of histidine (Hartman S. C. and R. C. Mulligan (1988) Proc. Natl. Acad. Sci. 85:8047–8051). Recently, the use of visible markers has gained popularity with such markers as anthocyanins, β glucuronidase, and its substrate, GUS, and luciferase and its substrate, luciferin, being widely used not only to identify transformants, but also to quantify the amount of transient or stable protein expression attributable to a specific vector system (Rhodes, C. A. et al. (1995) *Methods Mol. Biol.* 55:121–131).

Although the presence/absence of marker gene expression suggests that the gene of interest is also present, its presence and expression may need to be confirmed. For example, if the sequence encoding hPSHP is inserted within a marker gene sequence, recombinant cells containing sequences encoding hPSHP can be identified by the absence of marker gene function. Alternatively, a marker gene can be placed in tandem with an hPSHP sequence under the control of a single promoter. Expression of the marker gene in response to induction or selection usually indicates expression of the tandem hPSHP as well.

Alternatively, host cells which contain the coding sequence for hPSHP and express hPSHP may be identified by a variety of procedures known to those of skill in the art. These procedures include, but are not limited to, DNA-DNA or DNA-RNA hybridizations, fluorescent activated cell sorting and protein bioassay or immunoassay techniques which include membrane, solution, or chip based technologies for the detection and/or quantification of the nucleic acid or protein.

The presence of the polynucleotide sequence encoding hPSHP can be detected by DNA-DNA or DNA-RNA hybridization or amplification using probes or portions or fragments of polynucleotides encoding hPSHP. Nucleic acid amplification based assays involve the use of oligonucleotides or oligomers based on the hPSHP-encoding sequence to detect transfectants containing DNA or RNA encoding hPSHP. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides, which can be used as a probe or amplimer.

A variety of protocols for detecting and measuring the expression of hPSHP, using either polyclonal or monoclonal antibodies specific for the protein are known in the art. Examples include enzyme-linked immunosorbent assay (ELISA), radioimmunoassay (RIA), and fluorescent activated cell sorting (FACS). A two-site, monoclonal-based immunoassay utilizing monoclonal antibodies reactive to two non-interfering epitopes on hPSHP is preferred, but a competitive binding assay may be employed. These and other assays are described, among other places, in Hampton et al. (1990, *Serological Methods a Laboratory Manual,* APS Press, St Paul, Minn.) and Maddox et al. (1983) *J. Exp. Med.* 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding hPSHP include oligolabeling, nick translation, end-labeling or PCR amplification using a labeled nucleotide. Alternatively, the sequence encoding hPSHP, or any portion of it, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Pharmacia Upjohn, (Kalamazoo, Mich.); Promega (Madison, Wis.) and U.S. Biochemical Corp., Cleveland, Ohio). Suitable reporter molecules or labels, which may be used, include radionuclides, enzymes, fluorescent, chemiluminescent, or chromogenic agents as well as substrates, cofactors, inhibitors, magnetic particles, and the like.

Host cells transformed with a nucleotide sequence encoding hPSHP may be cultured under conditions suitable for the expression and recovery of the encoded protein from cell culture. The protein produced by a recombinant cell may be secreted or contained intracellularly depending on the sequence and/or the vector used. As will be understood by those of skill in the art, expression vectors containing polynucleotides which encode hPSHP may be designed to contain signal sequences which direct secretion of hPSHP through a prokaryotic or eukaryotic cell membrane. Other recombinant constructions may be used to join sequences encoding hPSHP to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle Wash.). The inclusion of a cleavable linker sequences such as those specific for Factor XA or enterokinase (Invitrogen, San Diego, Calif.) between the purification domain and hPSHP may be used to facilitate purification. One such expression vector which may be used provides for expression of a fusion protein containing a hPSHP and a nucleic acid encoding 6 histidine residues followed by thioredoxin and an enterokinase cleavage site. The histidine residues facilitate purification on IMIAC (immobilized metal ion affinity chromatography as described in Porath, J. et al. (1992) *Prot. Exp. Purif.* 3: 263–281) while the enterokinase cleavage site provides a means for purifying hPSHP from the fusion protein. A discussion of vectors which contain fusion proteins is provided in Kroll, D. J. et al. (1993) *DNA Cell Biol.* 12:441–453.

In addition to recombinant production, fragments of hPSHP may be produced by direct peptide synthesis using solid-phase techniques (cf Stewart et al. (1969) *Solid-Phase Peptide Synthesis,* W. H. Freeman Co., San Francisco, Calif.; Merrifield J. (1963) *J. Am. Chem. Soc.* 85:2149–2154). In vitro protein synthesis may be performed using manual techniques or by automation. Automated synthesis may be achieved, for example, using Applied Biosystems 431A Peptide Synthesizer (Perkin Elmer). Various fragments of hPSHP may be chemically synthesized separately and combined using chemical methods to produce the full length molecule.

THERAPEUTICS

In another embodiment of the invention, hPSHP or fragments thereof may be used for therapeutic purposes.

Based on the chemical and structural homology that exists among hPSHP protein (SEQ ID NO:1) and GI 162690 (SEQ ID NO:3), and GI 741603 (SEQ ID NO:4) hPSHP is believed to function in the signal transduction pathway of neurotransmitters in brain tissue and in cell development processes in peripheral organs. The similarities among the hPSHP (SEQ ID NO:1) and SEQ ID NO:3, and SEQ ID NO:4 protein sequences define hPSHP as a cAMP-regulated phosphoprotein, while the specific differences between hPSHP and SEQ ID NO:3, and SEQ ID NO:4 at their amino terminus indicate that hPSHP is a functionally distinct cAMP-regulated phosphoprotein (FIG. 2).

From the homology information provided above, it appears that hPSHP plays a role in the modulation of neurotransmitter signal transduction and cell development. Stimulation of hPSHP may enhance the survival of nerve cells and other tissues and contribute to their differentiation.

In one embodiment of the invention, the modulation of hPSHP by agonists and antagonists may play a role in reconstructing signal transduction pathways that have been interrupted by degenerative neuronal disease. Accordingly, in another embodiment of the s invention, hPSHP or derivatives thereof, may be used for regenerating and enhancing the survival of nerve cells by supplying hPSHP or stimulating residual hPSHP with hPSHP agonists to stop the degenerative process in certain brain diseases such as Parkinson's and Huntington's disease.

Control of hPSHP activity as a novel approach to degenerative neuronal disease treatment may be especially useful in combination therapy with other, conventional therapeutic agents. This is so because combinations of therapeutic agents having different cellular mechanisms of action often have synergistic effects allowing the use of lower effective doses of each agent thus lessening side effects.

In another therapeutic embodiment, antagonists which block or modulate the effect of hPSHP may be used in those situations where such inhibition or modulation is therapeutically desirable. Such situations may include the down-regulation of hPSHP activity to regulate cell growth or to suppress abnormal signal transduction in diseased tissue. For example, in one aspect, antibodies which are specific for hPSHP may be used as an agonist, antagonist, or as part of a targeting or delivery mechanism so as to bring a pharmaceutical agent to cells or tissue which express hPSHP.

The antibodies may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and other, may be immunized by injection with hPSHP or any fragment or oligopeptide thereof which has properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the peptides, fragments, or oligopeptides used to induce antibodies to hPSHP have an amino acid sequence consisting of at least five amino acids, and more preferably at least 10 amino acids. It is also preferable that they are identical to a portion of the amino acid sequence of the natural protein, and they may contain the entire amino acid sequence of a small, naturally occurring molecule. Short stretches of hPSHP amino acids may be fused with those of another protein such as keyhole limpet hemocyanin and antibody produced against the chimeric molecule.

Monoclonal antibodies to hPSHP may be prepared using any technique which provides for the production of antibody molecules by continuous cell lines in culture. These include, but are not limited to, the hybridoma technique, the human B-cell hybridoma technique, and the EBV-hybridoma technique (Koehler et al. (1975) Nature 256:495–497; Kosbor et al. (1983) Immunol. Today 4:72; Cote et al. (1983) Proc. Natl. Acad. Sci. 80:2026–2030; Cole et al. (1985) *Monoclonal Antibodies and Cancer Therapy*, Alan R. Liss Inc., New York, N.Y., pp. 77–96).

In addition, techniques developed for the production of "chimeric antibodies", the splicing of mouse antibody genes to human antibody genes to obtain a molecule with appropriate antigen specificity and biological activity can be used (Morrison et al. (1984) Proc. Natl. Acad. Sci. 81:6851–6855; Neuberger et al. (1984) Nature 312:604–608; Takeda et al. (1985) Nature 314:452–454). Alternatively, techniques described for the production of single chain antibodies may be adapted, using methods known in the art, to produce hPSHP-specific single chain antibodies. Antibodies with related specificity but of distinct idiotypic composition may be generated by chain shuffling from random combinatorial immunoglobin libraries (Burton D. R. (1991) Proc. Natl. Acad. Sci. 88:11120–3).

Antibodies may also be produced by inducing in vivo production in the lymphocyte population or by screening recombinant immunoglobulin libraries or panels of highly specific binding reagents as disclosed in the literature (Orlandi et al. (1989) Proc. Natl. Acad. Sci. 86: 3833–3837 and Winter et al. (1991), Nature 349:293–299).

Antibody fragments which contain specific binding sites for hPSHP may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse et al. (1989) Science 256:1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between hPSHP and its specific antibody. A two-site, monoclonal-based immunoassay utilizing monoclonal antibodies reactive to two non-interfering epitopes on a specific hPSHP protein is preferred, but a competitive binding assay may also be employed (Maddox et al. (1983) J. Exp. Med. 158:1211).

In another embodiment of the invention, the polynucleotides encoding hPSHP, or any fragment thereof or antisense sequences, may be used for therapeutic purposes. In one aspect, antisense to the polynucleotide encoding hPSHP may be used in situations in which it would be desirable to block the biological activity of hPSHP. In particular, cells may be transformed with antisense sequences to polynucleotides encoding hPSHP. Thus, antisense sequences may be used to or to achieve regulation of gene function. Such technology is now well known in the art, and sense or antisense oligomers, or larger fragments, can be designed from various locations along the coding or control regions.

Expression vectors derived from retroviruses, adenovirus, herpes or vaccinia viruses, or from various bacterial plasmids, may be used for delivery of nucleotide sequences to the targeted organ, tissue, or cell population. Methods which are well known to those skilled in the art can be used to construct recombinant vectors which will express antisense polynucleotides of the gene encoding hPSHP. See, for example, the techniques described in Sambrook et al. (supra) and Ausubel et al. (supra).

Genes encoding hPSHP can be turned off by transfecting a cell or tissue with expression vectors which express high levels of a polynucleotide or fragment thereof which encodes hPSHP. Such constructs may be used to introduce untranslatable sense or antisense sequences into a cell. Even in the absence of integration into the DNA, such vectors may continue to transcribe RNA molecules until all copies are disabled by endogenous nucleases. Transient expression may last for a month or more with a non-replicating vector and even longer if appropriate replication elements are part of the vector system.

As mentioned above, modifications of gene expression can be obtained by designing antisense molecules, DNA, RNA, or PNA, to the control regions of gene encoding hPSHP, i.e., the promoters, enhancers, and introns. Oligonucleotides derived from the transcription initiation site, e.g., between −10 and +10 regions of the leader sequence, are preferred. The antisense molecules may also be designed to block translation of mRNA by preventing the transcript from binding to ribosomes. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee et al., (1994) *Molecular and Immunologic Approaches,* Futura Publishing Co., Mt. Kisco, N.Y.).

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding hPSHP.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of RNA molecules. These include techniques for chemically synthesizing oligonucleotides such as solid phase phosphoramidite chemical synthesis. Alternatively, RNA molecules may be generated by in vitro and in vivo transcription of DNA sequences encoding hPSHP. Such DNA sequences may be incorporated into a wide variety of vectors with suitable RNA polymerase promoters such as T7 or SP6. Alternatively, antisense cDNA constructs that synthesize antisense RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Methods for introducing vectors into cells or tissues include those methods discussed above. These methods are equally suitable for use in in vivo, in vitro, and ex vivo therapy. For ex vivo therapy, vectors may be introduced into stem cells taken from the patient and clonally propagated for autologous transplant back into that same patient. Delivery by transfection and by liposome injections may be achieved using methods which are well known in the art.

Any of the therapeutic methods described above may be applied to any suitable subject including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of hPSHP, antibodies to hPSHP, mimetics, agonists, antagonists, or inhibitors of hPSHP. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, transdermal, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Pharmaceutical formulations suitable for parenteral administration may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1 mM–50 mM histidine, 0.1%–2% sucrose, and 2%–7% mannitol at a pH range of 4.5 to 5.5 that is/are combined with buffer prior to use.

After pharmaceutical compositions have been prepared, they can be placed in an appropriate container and labeled for treatment of an indicated condition. For administration of hPSHP, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal models, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example hPSHP or fragments thereof, agonists antibodies to hPSHP or agonists, antagonists, or inhibitors of hPSHP, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject which requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

DIAGNOSTICS

In another embodiment, antibodies which are specific for hPSHP may be used for the diagnosis of conditions or diseases characterized by expression of hPSHP, or in assays to monitor patients being treated with hPSHP, agonists, antagonists or inhibitors. The antibodies useful for diagnostic purposes may be prepared in the same manner as those described above for therapeutics. Diagnostic assays for hPSHP include methods which utilize the antibody and a label to detect hPSHP in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols for measuring hPSHP, using either polyclonal or monoclonal antibodies specific for the respective protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on hPSHP is preferred, but a competitive binding assay may be employed.

In order to provide a basis for diagnosing abnormal levels of hPSHP expression, normal or standard values for hPSHP expression are established. This may be accomplished by combining body fluids or cell extracts taken from normal mammalian subjects, preferably human, with antibody to hPSHP under conditions suitable for complex formation which are well known in the art. The amount of standard complex formation may be quantified by comparing various artificial membranes containing known quantities of hPSHP with both control and disease samples from biopsied tissues. Then, standard values obtained from normal samples may be compared with values obtained from samples from subjects which are symptomatic for the disease. Deviation between standard and subject values establishes the parameters for diagnosing the disease.

In another embodiment of the invention, the polynucleotides encoding hPSHP may be used for diagnostic purposes. The polynucleotides which may be used include oligonucleotide sequences, antisense RNA and DNA molecules, and PNAs. The polynucleotides may be used to detect and quantitate gene expression in biopsied tissues in which expression of hPSHP may be implicated. The diagnostic assay may be used to distinguish between absence, presence, and excess expression of hPSHP, and to monitor regulation of hPSHP levels during therapeutic intervention.

In one aspect, hybridization or PCT probes which are capable of detecting polynucleotide sequences, including genomic sequences, encoding hPSHP or closely related molecules, may be used to identify nucleic acid sequences which encode hPSHP. The specificity of the probe, whether it is made from a highly specific region, e.g., 10 unique nucleotides in the 5' regulatory region, or a less specific region, e.g., especially in the 3' region, and the stringency of the hybridization or amplification (maximal, high, intermediate, or low) will determine whether the probe identifies only naturally occurring sequences encoding hPSHP, alleles, or related sequences.

Probes may also be used for the detection of related sequences, and should preferably contain at least 50% of the nucleotides from any of these hPSHP encoding sequences. The hybridization probes of the subject invention may be derived from the nucleotide sequence of SEQ ID NO:2 or from genomic sequence including promoter, enhancer elements, and introns of the naturally occurring hPSHP.

Other means for producing specific hybridization probes for DNAs encoding hPSHP include the cloning of nucleic acid sequences encoding hPSHP or hPSHP derivatives into vectors for the production of mRNA probes. Such vectors are known in the art, commercially available, and may be used to synthesize RNA probes in vitro by means of the addition of the appropriate RNA polymerase as T7 or SP6 RNA polymerase and the appropriate radioactively labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like.

Polynucleotide sequences encoding hPSHP may be used for the diagnosis of conditions or diseases which are associated with expression of hPSHP. The polynucleotide sequences encoding hPSHP may be used in hybridization or PCR assays of fluids or tissues from patient biopsies to detect hPSHP expression. The form of such qualitative or quantitative methods may include Southern or northern analysis, dot blot, or other membrane-based technologies; PCR technologies; dip stick, pin, chip, and ELISA, all methods which are well known in the art.

In a particular aspect, the nucleotide sequences encoding hPSHP may be useful in assays that detect activation or inactivation associated with various degenerative neuronal diseases. The nucleotide sequence encoding hPSHP may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly elevated over that of a comparable control sample, the nucleotide sequence has hybridized with nucleotide sequences in the sample, and the presence of elevated levels of nucleotide sequences encoding hPSHP in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of hPSHP, a normal or standard profile for expression is established. This may be accomplished by combining body fluids or cell extracts taken from normal subjects, either animal or human, with hPSHP, or a fragment thereof, under conditions suitable for hybridization or amplification. Standard hybridization may be quantified by comparing the values obtained from normal subjects with a dilution series of hPSHP measured in the same experiment, where a known amount of a substantially purified hPSHP is used. Standard values obtained from normal samples may be compared with values obtained from samples from patients who are symptomatic for disease associated with hPSHP. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

Additional diagnostic uses for oligonucleotides encoding hPSHP may involve the use of PCR. Such oligomers may be chemically synthesized, generated enzymatically, or produced from a recombinant source. Oligomers will preferably consist of two nucleotide sequences, one with sense orientation (5'→3') and another with antisense (3'←5'), employed under optimized conditions for identification of a specific gene or condition. The same two oligomers, nested sets of oligomers, or even a degenerate pool of oligomers may be employed under less stringent conditions for detection and/ or quantitation of closely related DNA or RNA sequences.

Methods which may also be used to quantitate the expression of hPSHP include radiolabeling or biotinylating nucleotides, coamplification of a control nucleic acid, and standard curves onto which the experimental results are interpolated (Melby, P. C. et al. (1993) J. Immunol. Methods, 159:235–244; Duplaa, C. et al. (1993) Anal. Biochem. 229–236.) The speed of quantitation of multiple samples may be accelerated by running the assay in an ELISA format where the oligomer of interest is presented in various dilutions and a spectrophotometric or calorimetric response gives rapid quantitation.

In other embodiments of the invention, the nucleotide sequences of the invention may be used in molecular biology techniques that have not yet been developed, provided the new techniques rely on properties of nucleotide sequences that are currently known, such as the triplet genetic code, specific base pair interactions, and the like.

In another embodiment of the invention, the nucleic acid sequence which encodes hPSHP may also be used to generate hybridization probes which are useful for mapping the naturally occurring genomic sequence. The sequence may be mapped to a particular chromosome or to a specific region of the chromosome using well known techniques. Such techniques include in situ hybridization to chromosomal spreads, flow-sorted chromosomal preparations, or artificial chromosome constructions, such as yeast artificial chromosomes, bacterial artificial chromosomes, bacterial P1 constructions or single chromosome cDNA libraries as reviewed in Price C. M. (1993) Blood Rev. 7:127–134, and Trask B. J. (1991) Trends Genet 7:149–154.

The technique of fluorescent in situ hybridization of chromosome spreads, as described in Verma et al. (1988) *Human Chromosomes: A Manual of Basic Techniques*, Pergamon Press, New York, N.Y., may also be used. Fluorescent in situ hybridization of chromosomal preparations and other physical chromosome mapping techniques may be correlated with additional genetic map data. Examples of genetic map data can be found in the 1994 Genome Issue of Science (265:1981f). Correlation between the location of the gene encoding hPSHP on a physical chromosomal map and a specific disease (or predisposition to a specific disease) may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22–23 (Gatti et al. (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, hPSHP, its catalytic or immunogenic fragments or oligopeptides thereof, can be used for screening libraries of compounds in any of a variety of drug screening techniques. The fragment employed in such a test may be free in solution, affixed to a solid support, borne on a cell surface, or located intracellularly. The formation of binding complexes, between hPSHP and the agent being tested, may be measured.

Another technique for drug screening which may be used provides for high throughput screening of compounds having suitable binding affinity to the protein of interest as described in published PCT application WO84/03564. In this method, as applied to hPSHP, large numbers of different small test compounds are synthesized on a solid substrate, such as plastic pins or some other surface. The test compounds are reacted with hPSHP, or fragments thereof, and washed. Bound hPSHP is then detected by methods well known in the art. Purified hPSHP can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding hPSHP specifically compete with a test compound for binding hPSHP. In this manner, the antibodies can be used to detect the presence of any peptide which shares one or more antigenic determinants with hPSHP.

In additional embodiments, the nucleotide sequences which encode hPSHP may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I HNT2RAT01 cDNA Library Construction

The hNT2 cell line exhibits characteristics of a committed neuronal precursor cell which is at an early stage of development. The hNT2 cell line can be induced by retinoic acid (RA) to differentiate, as described in Andrews PW (1984) *Dev Biol* 103:285–293. cDNA libraries are available for the untreated hNT2 cell line (HNT2NOT1, Cat. No. 937230), for hNT2 cells treated with RA for 24 hours (HNT2RAT1, Cat. No. 937231), and for the hNT2-N cell line (HNT2AGT1, Cat. No. 937233) by Stratagene (Stratagene, La Jolla Calif.).

For purposes of this invention, hNT2 cells were induced with RA. The method used in the present invention involved suspending hNT2 cells in Dulbecco's modified Eagle's medium (DMEM) including 10% fetal bovine serum and penicillin/ streptomycin, and treating the cells with 10 $\mu$M RA for 24 hours. This procedure created cells whose differentiation process likely has commenced. These cells were used for the HNT2RAT1 cell line.

The HNT2RAT1 cDNA library was constructed essentially as described below. Stratagene isolated the mRNA. First strand cDNA synthesis was accomplished using an oligo d(T) primer/linker which also contained an XhoI restriction site. Second strand synthesis was performed using a combination of DNA polymerase I, *E. coli* ligase and RNase H, followed by the addition of an EcoRI adaptor to the blunt ended cDNA. The EcoRI adapted, double-stranded cDNA was then digested with XhoI restriction enzyme and fractionated to obtain sequences which exceeded 800 bp in size. The cDNAs were inserted into the LambdaZap® vector system (Stratagene); then the vector which contains the pBluescript™ phagemid (Stratagene) was transformed into *E. coli* host cells strain XL 1-BlueMRF™ (Stratagene).

The phagemid forms of individual cDNA clones were obtained by the in vivo excision process. Enzymes from both pBluescript and a cotransformed f1 helper phage nicked the DNA, initiated new DNA synthesis, and created the smaller, single-stranded circular phagemid molecules which contained the cDNA insert. The phagemid DNA was released, purified, and used to reinfect fresh host cells (SOLR, Stratagene). Presence of the phagemid which carries the gene for β-lactamase allowed transformed bacteria to grow on medium containing ampicillin.

II Isolation and Sequencing of cDNA Clones

Plasmid DNA was released from the cells and purified using the Miniprep Kit (Catalogue #77468; Advanced Genetic Technologies Corporation, Gaithersburg Md.). This kit consists of a 96 well block with reagents for 960 purifications. The recommended protocol was employed except for the following changes: 1) the 96 wells were each filled with only 1 ml of sterile Terrific Broth (Catalog #22711, LIFE TECHNOLOGIES™, Gaithersburg Md.) with carbenicillin at 25 mg/L and glycerol at 0.4%; 2) the bacteria were cultured for 24 hours after the wells were inoculated and then lysed with 60 μl of lysis buffer; 3) a centrifugation step employing the Beckman GS-6R @2900 rpm for 5 min was performed before the contents of the block were added to the primary filter plate; and 4) the optional step of adding isopropanol to TRIS buffer was not routinely performed. After the last step in the protocol, samples were transferred to a Beckman 96-well block for storage.

Alternative methods of purifying plasmid DNA include the use of MAGIC MINIPREPS™ DNA Purification System (Catalogue #A7100, Promega, Madison Wis.) or QIAwell™-8 Plasmid, QIAwell PLUS DNA and QIAwell ULTRA DNA Purification Systems (QIAGEN® Chatsworth Calif.).

The cDNAs were sequenced by the method of Sanger F and A R Coulson (1975; J Mol Biol 94:441f), using a Hamilton Micro Lab 2200 (Hamilton, Reno Nev.) in combination with four Peltier Thermal Cyclers (PTC200 from MJ Research, Watertown Mass.) and Applied Biosystems 377 or 373 DNA Sequencing Systems (Perkin Elmer) and reading frame was determined.

III Homology Searching of cDNA Clones and Their Deduced Proteins

Each cDNA was compared to sequences in GenBank using a search algorithm developed by Applied Biosystems and incorporated into the INHERIT™ 670 Sequence Analysis System. In this algorithm, Pattern Specification Language (TRW Inc, Los Angeles, Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT-670 Sequence Analysis System using the methods similar to those used in DNA sequence homologies. Pattern Specification Language and parameter windows were used to search protein databases for sequences containing regions of homology which were scored with an initial value. Dot-matrix homology plots were examined to distinguish regions of significant homology from chance matches.

BLAST, which stands for Basic Local Alignment Search Tool (Altschul S F (1993) J. Mol. Evol. 36:290–300; Altschul et al. (1990) J. Mol. Biol. 215:403–410), was used to search for local sequence alignments. BLAST produces alignments of both nucleotide and amino acid sequences to determine sequence similarity. Because of the local nature of the alignments, BLAST is especially useful in determining exact matches or in identifying homologs. BLAST is useful for matches which do not contain gaps. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for hPSHP between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an hPSHP within the context of the entire database search. Any database sequence whose match satisfies E is reported in the program output.

IV Northern Analysis

Northern analysis is a laboratory technique used to detect the presence of a transcript of a gene and involves the hybridization of a labeled nucleotide sequence to a membrane on which RNAs from a particular cell type or tissue have been bound (Sambrook et al., supra).

Analogous computer techniques using BLAST (Altschul S. F. 1993 and 1990, supra) are used to search for identical or related molecules in nucleotide databases such as GenBank or the LIFESEQ™ database (Incyte Pharmaceuticals, Inc., Palo Alto, Calif.). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\% \text{ sequence identity} \times \% \text{ maximum BLAST score}}{100}$$

and it takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

V Extension of hPSHP-Encoding Polynucleotides to Full Length or to Recover Regulatory Elements Full length hPSHP-encoding nucleic acid sequence (SEQ ID NO:2) is used to design oligonucleotide primers for extending a partial nucleotide sequence to full length or for obtaining 5' sequences from genomic libraries. One primer is synthesized to initiate extension in the antisense direction (XLR) and the other is synthesized to extend sequence in the sense direction (XLF). Primers are used to facilitate the extension of the known hPSHP-encoding sequence "outward" generating amplicons containing new, unknown nucleotide sequence for the region of interest. The initial primers are designed from the cDNA using OLIGO® 4.06 Primer Analysis Software (National Biosciences), or another appropriate program, to be 22–30 nucleotides in length, to have a GC content of 50% or more, and to anneal to the target sequence at temperatures about 68°–72° C. Any stretch of nucleotides which would result in hairpin structures and primer-primer dimerizations is avoided.

The original, selected cDNA libraries, or a human genomic library are used to extend the sequence; the latter is most useful to obtain 5' upstream regions. If more extension is necessary or desired, additional sets of primers are designed to further extend the known region.

By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the Peltier Thermal Cycler (PTC200; M. J. Research, Watertown, Mass.) and the following parameters:

| Step 1  | 94° C. for 1 min (initial denaturation) |
|---------|------------------------------------------|
| Step 2  | 65° C. for 1 min                         |
| Step 3  | 68° C. for 6 min                         |
| Step 4  | 94° C. for 5 sec                         |
| Step 5  | 65° C. for 1 min                         |
| Step 6  | 68° C. for 7 min                         |
| Step 7  | Repeat step 4–6 for 15 additional cycles |
| Step 8  | 94° C. for 15 sec                        |
| Step 9  | 65° C. for 1 min                         |
| Step 10 | 68° C. for 7:15 min                      |
| Step 11 | Repeat step 8–10 for 12 cycles           |
| Step 12 | 72° C. for 8 min                         |
| Step 13 | 4° C. (and holding)                      |

A 5–10 µl aliquot of the reaction mixture is analyzed by electrophoresis on a low concentration (about 0.6–0.8%) agarose mini-gel to determine which reactions were successful in extending the sequence. Bands thought to contain the largest products are selected and cut out of the gel. Further purification involves using a commercial gel extraction method such as QIAQuick™ (QIAGEN Inc., Chatsworth, Calif.). After recovery of the DNA, Klenow enzyme is used to trim single-stranded, nucleotide overhangs creating blunt ends which facilitate religation and cloning.

After ethanol precipitation, the products are redissolved in 13 µl of ligation buffer, 1 µl T4-DNA ligase (15 units) and 1 µl T4 polynucleotide kinase are added, and the mixture is incubated at room temperature for 2–3 hours or overnight at 16° C. Competent *E. coli* cells (in 40 µl of appropriate media) are transformed with 3 µl of ligation mixture and cultured in 80 µl of SOC medium (Sambrook et al., supra). After incubation for one hour at 37° C., the whole transformation mixture is plated on Luria Bertani (LB)-agar (Sambrook et al., supra) containing 2xCarb. The following day, several colonies are randomly picked from each plate and cultured in 150 µl of liquid LB/2xCarb medium placed in an individual well of an appropriate, commercially-available, sterile 96-well microtiter plate. The following day, 5 µl of each overnight culture is transferred into a non-sterile 96-well plate and after dilution 1:10 with water, 5 µl of each sample is transferred into a PCR array.

For PCR amplification, 18 µl of concentrated PCR reaction mix (3.3x) containing 4 units of rTth DNA polymerase, a vector primer, and one or both of the gene specific primers used for the extension reaction are added to each well. Amplification is performed using the following conditions:

| Step 1 | 94° C. for 60 sec                         |
|--------|-------------------------------------------|
| Step 2 | 94° C. for 20 sec                         |
| Step 3 | 55° C. for 30 sec                         |
| Step 4 | 72° C. for 90 sec                         |
| Step 5 | Repeat steps 2–4 for an additional 29 cycles |
| Step 6 | 72° C. for 180 sec                        |
| Step 7 | 4° C. (and holding)                       |

Aliquots of the PCR reactions are run on agarose gels together with molecular weight markers. The sizes of the PCR products are compared to the original partial cDNAs, and appropriate clones are selected, ligated into plasmid, and sequenced.

VI Labeling and Use of Hybridization Probes

Hybridization probes derived from SEQ ID NO:2 are employed to screen cDNAs, genomic DNAs, or mRNAs. Although the labeling of oligonucleotides, consisting of about 20 base-pairs, is specifically described, essentially the same procedure is used with larger cDNA fragments. Oligonucleotides are designed using state-of-the-art software such as OLIGO 4.06 (National Biosciences), labeled by combining 50 pmol of each oligomer and 25 mCi of $[\gamma\text{-}^{32}P]$ adenosine triphosphate (Amersham, Chicago, Ill.) and T4 polynucleotide kinase (DuPont NEN®, Boston, Mass.). The labeled oligonucleotides are substantially purified with Sephadex G-25 superfine resin column (Pharmacia). A portion containing $10^7$ counts per minute of each of the sense and antisense oligonucleotides is used in a typical membrane based hybridization analysis of human genomic DNA digested with one of the following endonucleases (Ase I, Bgl II, Eco RI, Pst I, Xba 1, or Pvu II; DuPont NEN®).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1x saline sodium citrate and 0.5% sodium dodecyl sulfate. After XOMAT AR™ film (Kodak, Rochester, N.Y.) is exposed to the blots in a Phosphoimager cassette (Molecular Dynamics, Sunnyvale, Calif.) for several hours, hybridization patterns are compared visually.

VII Antisense Molecules

The hPSHP-encoding sequence, or any part thereof, is used to inhibit in vivo or in vitro expression of naturally occurring hPSHP. Although use of antisense oligonucleotides, comprising about 20 base-pairs, is specifically described, essentially the same procedure is used with larger cDNA fragments. An oligonucleotide based on the coding sequences of hPSHP as shown in FIG. 1, is used to inhibit expression of naturally occurring hPSHP. The complementary oligonucleotide is designed from the most unique 5' sequence as shown in FIG. 1 and used either to inhibit transcription by preventing promoter binding to the upstream nontranslated sequence or translation of an hPSHP-encoding transcript by preventing the ribosome from binding. Using an appropriate portion of the leader and 5' sequence of SEQ ID NO:2, an effective antisense oligonucleotide includes any 15–20 nucleotides spanning the region which translates into the signal or early coding sequence of the polypeptide as shown in FIG. 1.

VIII Expression of hPSHP

Expression of the hPSHP is accomplished by subcloning the cDNAs into appropriate vectors and transforming the vectors into host cells. In this case, the cloning vector, pSport, previously used for the generation of the cDNA library is used to express hPSHP in *E. coli*. Upstream of the cloning site, this vector contains a promoter for β-galactosidase, followed by sequence containing the amino-terminal Met, and the subsequent seven residues of β-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first seven residues of β-galactosidase, about 5 to 15 residues of linker, and the full length hPSHP-encoding sequence. The signal sequence directs the secretion of hPSHP into the bacterial growth media which can be used directly in the following assay for activity.

IX Demonstration of hPSHP Activity

The characterization of hPSHP activity and specificity is based on its ability to be phosphorylated by cAMP-dependent protein kinase. Isolated native hPSHP protein, cell fractions containing hPSHP, or recombinantly produced hPSHP are used in phosphorylation assays to establish the specificity, selectivity, and site of phosphorylation. Phosphorylation reactions containing 50 mM Hepes (ph 7.4), 10 mM magnesium acetate, 1 mM EGTA, 5 μM (g-32P)ATP, the hPSHP protein and 0.1–0.2 μg of the catalytic subunit of cAMP-dependent protein kinase are incubated for 45 minutes at 30° C. The reaction is stopped; samples can be removed for immunoprecipitation, gel electrophoresis and autoradiography, and direct measurement of the incorporated 32P on a scintillation counter (Girault, J. A. Proc. Natl. Acad. Sci. (1988) 85:7790–7794).

X Production of hPSHP Specific Antibodies hPSHP that is substantially purified using PAGE electrophoresis (Sambrook, supra), or other purification techniques, is used to immunize rabbits and to produce antibodies using standard protocols. The amino acid sequence translated from hPSHP is analyzed using DNASTAR software (DNASTAR Inc) to determine regions of high immunogenicity and a corresponding oligopolypeptide is synthesized and used to raise antibodies by means known to those of skill in the art. Analysis to select appropriate epitopes, such as those near the C-terminus or in hydrophilic regions such as that described by Ausubel et al. (supra), may be used.

Typically, the oligopeptides are 15 residues in length, synthesized using an Applied Biosystems Peptide Synthesizer Model 431A using fmoc-chemistry, and coupled to keyhole limpet hemocyanin (KLH, Sigma St. Louis Mo.) by reaction with N-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

XI Purification of Naturally Occurring hPSHP Using Specific Antibodies

Naturally occurring or recombinant hPSHP is substantially purified by immunoaffinity chromatography using antibodies specific for hPSHP. An immunoaffinity column is constructed by covalently coupling hPSHP antibody to an activated chromatographic resin, such as CnBr-activated Sepharose (Pharmacia Biotech). After the coupling, the resin is blocked and washed according to the manufacturer's instructions.

Media containing hPSHP is passed over the immunoaffinity column, and the column is washed under conditions that allow the preferential absorbance of hPSHP (e.g., high ionic strength buffers in the presence of detergent). The column is eluted under conditions that disrupt antibody/hPSHP binding (eg, a buffer of pH 2–3 or a high concentration of a chaotrope, such as urea or thiocyanate ion), and hPSHP is collected.

XII Identification of Molecules Which Interact with hPSHP hPSHP, or biologically active fragments thereof, are labeled with $^{125}$I Bolton-Hunter reagent (Bolton et al. (1973) Biochem. J. 133: 529). Candidate molecules previously arrayed in the wells of a multi-well plate are incubated with the labeled hPSHP, washed and any wells with labeled hPSHP complex are assayed. Data obtained using different concentrations of hPSHP are used to calculate values for the number, affinity, and association of hPSHP with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. An isolated and purified polynucleotide consisting of SEQ ID NO:2.

2. An isolated and purified polynucleotide consisting of the nucleic acid sequence which is completely complementary to the polynucleotide of claim 1.

* * * * *

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 118 amino acids
      (B) TYPE: amino acid
      (C) STRANDEDNESS: single
      (D) TOPOLOGY: linear (vii) IMMEDIATE SOURCE:
      (A) LIBRARY:
      (B) CLONE: Consensus (xi) SEQUENCE DESCRIPTION: SEQ ID NO:1:

Met Ala Gly Gly Leu Gly Cys Glu Cys Val Leu Val Cys Arg Gly
1               5                   10                  15

His Ala Gly Ala Lys Lys Val Phe Cys Leu Arg Arg Ala Glu Glu Ala
            20                  25                  30

Lys Leu Lys Ala Lys Tyr Pro Ser Leu Gly Gln Lys Pro Gly Gly Ser
        35                  40                  45

Asp Phe Leu Met Lys Arg Leu Gln Lys Gly Gln Lys Tyr Phe Asp Ser
    50                  55                  60

Gly Asp Tyr Asn Met Ala Lys Ala Lys Met Lys Asn Lys Gln Leu Pro
65                  70                  75                  80

Ser Ala Gly Pro Asp Lys Asn Leu Val Thr Gly Asp His Ile Pro Thr
                85                  90                  95

Pro Gln Asp Leu Pro Gln Arg Lys Ser Ser Leu Val Thr Ser Lys Leu
            100                 105                 110

Ala Gly Gly Gln Val Glu
        115

(2) INFORMATION FOR SEQ ID NO:2:

(i) SEQUENCE CHARACTERISTICS:
        (A) LENGTH: 454 base pairs
        (B) TYPE: nucleic acid
        (C) STRANDEDNESS: single
        (D) TOPOLOGY: linear (vii) IMMEDIATE SOURCE:
        (A) LIBRARY:
        (B) CLONE: Concensus (xi) SEQUENCE DESCRIPTION: SEQ ID NO:2:

GGTGAATGGA AAGGGGATGG CTGGTGGTCT TGGGTGTGAA TGTGTGTTAT TGGTTTGTAG      60

AGGACACGCA GGAGCAAAGA AGGTATTCTG CCTGAGAAGA GCTGAAGAGG CAAAGCTAAA     120

GGCCAAATAC CCAAGCCTAG GACAAAAGCC TGGAGGCTCC GACTTTCTCA TGAAGAGACT     180

CCAGAAAGGG CAAAAGTACT TTGACTCAGG AGACTACAAC ATGGCCAAAG CCAAGATGAA     240

GAATAAGCAG CTGCCAAGTG CAGGACCAGA CAAGAACCTG GTGACTGGTG ATCACATCCC     300

CACCCCACAG GATCTGCCCC AGAGAAAGTC CTCGCTCGTC ACCAGCAAGC TTGCGGGTGG     360

CCAAGTTGAA TGATGCTGCC CGGGGCTCTG CCAGATCCTG AGACGCTTCC CCTCCCTGCN     420

CCACCCGGGT CCTGTGCTGG CTCCTGCCCC TTCC                                 454

(2) INFORMATION FOR SEQ ID NO:3:

(i) SEQUENCE CHARACTERISTICS:
        (A) LENGTH: 112 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 162690

(xi) SEQUENCE DESCRIPTION: SEQ ID NO:3:

Met Ser Ala Glu Val Pro Glu Ala Ala Ser Ala Glu Glu Gln Lys Glu
1               5                   10                  15

Met Glu Asp Lys Val Thr Ser Pro Glu Lys Ala Glu Glu Ala Lys Leu
            20                  25                  30

Lys Ala Arg Tyr Pro His Leu Gly Gln Lys Pro Gly Gly Ser Asp Phe

```
                        35            40              45
Leu Arg Lys Arg Leu Gln Lys Gly Gln Lys Tyr Phe Asp Ser Gly Asp
    50              55              60

Tyr Asn Met Ala Lys Ala Lys Met Lys Asn Lys Gln Leu Pro Thr Ala
65              70              75              80

Thr Pro Asp Lys Thr Glu Val Thr Gly Asp His Ile Pro Thr Pro Gln
            85              90              95

Asp Leu Pro Gln Arg Lys Pro Ser Leu Val Ala Ser Lys Leu Ala Gly
            100             105             110

(2) INFORMATION FOR SEQ ID NO:4:

(i) SEQUENCE CHARACTERISTICS:
        (A) LENGTH: 96 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 741603

(xi) SEQUENCE DESCRIPTION: SEQ ID NO:4:

Met Glu Asp Lys Val Thr Ser Pro Glu Lys Ala Glu Glu Ala Lys Leu
1               5               10              15

Lys Ala Arg Tyr Pro His Leu Gly Gln Lys Pro Gly Gly Ser Asp Phe
            20              25              30

Leu Arg Lys Arg Leu Gln Lys Gly Gln Lys Tyr Phe Asp Ser Gly Asp
            35              40              45

Tyr Asn Met Ala Lys Ala Lys Met Lys Asn Lys Gln Leu Pro Thr Ala
50              55              60

Ala Pro Asp Lys Thr Glu Val Thr Gly Asp His Ile Pro Thr Pro Gln
65              70              75              80

Asp Leu Pro Gln Arg Lys Pro Ser Leu Val Ala Ser Lys Leu Ala Gly
            85              90              95
```